United States Patent
Hornegger et al.

(10) Patent No.: US 7,020,235 B2
(45) Date of Patent: Mar. 28, 2006

(54) METHOD FOR GENERATING A VOLUME DATASET

(75) Inventors: Joachim Hornegger, Baiersdorf (DE); Siegfried Schneider, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 169 days.

(21) Appl. No.: 10/651,364

(22) Filed: Aug. 29, 2003

(65) Prior Publication Data

US 2004/0066906 A1    Apr. 8, 2004

(30) Foreign Application Priority Data

Sep. 5, 2002    (DE)    ................ 102 41 184

(51) Int. Cl.
*A61B 6/03*    (2006.01)

(52) U.S. Cl. .......................... 378/9; 378/901
(58) Field of Classification Search ................ 378/4, 378/8, 9, 15, 19, 901

See application file for complete search history.

(56) References Cited

U.S. PATENT DOCUMENTS

| 4,196,352 | A | * | 4/1980 | Berninger et al. | ............. 378/7 |
| 5,068,882 | A | * | 11/1991 | Eberhard | ........................ 378/4 |
| 5,375,156 | A | * | 12/1994 | Kuo-Petravic et al. | ......... 378/9 |
| 5,515,416 | A |   | 5/1996 | Siczek | .......................... 378/197 |
| 5,923,721 | A |   | 7/1999 | Duschka | ....................... 378/92 |
| 6,421,412 | B1 | * | 7/2002 | Hsieh et al. | .................... 378/9 |
| 6,873,677 | B1 | * | 3/2005 | Kaufman | ........................ 378/4 |

* cited by examiner

*Primary Examiner*—David V Bruce
(74) *Attorney, Agent, or Firm*—Schiff Hardin LLP

(57) ABSTRACT

In a method for generating a volume dataset of a subject with a first X-ray system having an X-ray source and an X-ray receiver and with a second X-ray system having an X-ray source and an X-ray receiver, the first X-ray system is rotated around an axis and sweeps a first angular range. Substantially simultaneously, a second series of 2D projections of the subject is acquired with the second X-ray system at projection angles differing from one another, by the second X-ray system being rotated around an axis and sweeping a second angular range differing from the first angular range. A volume dataset of the subject is generated from the first and second series of 2D projections of the subject acquired by the two X-ray systems.

9 Claims, 2 Drawing Sheets

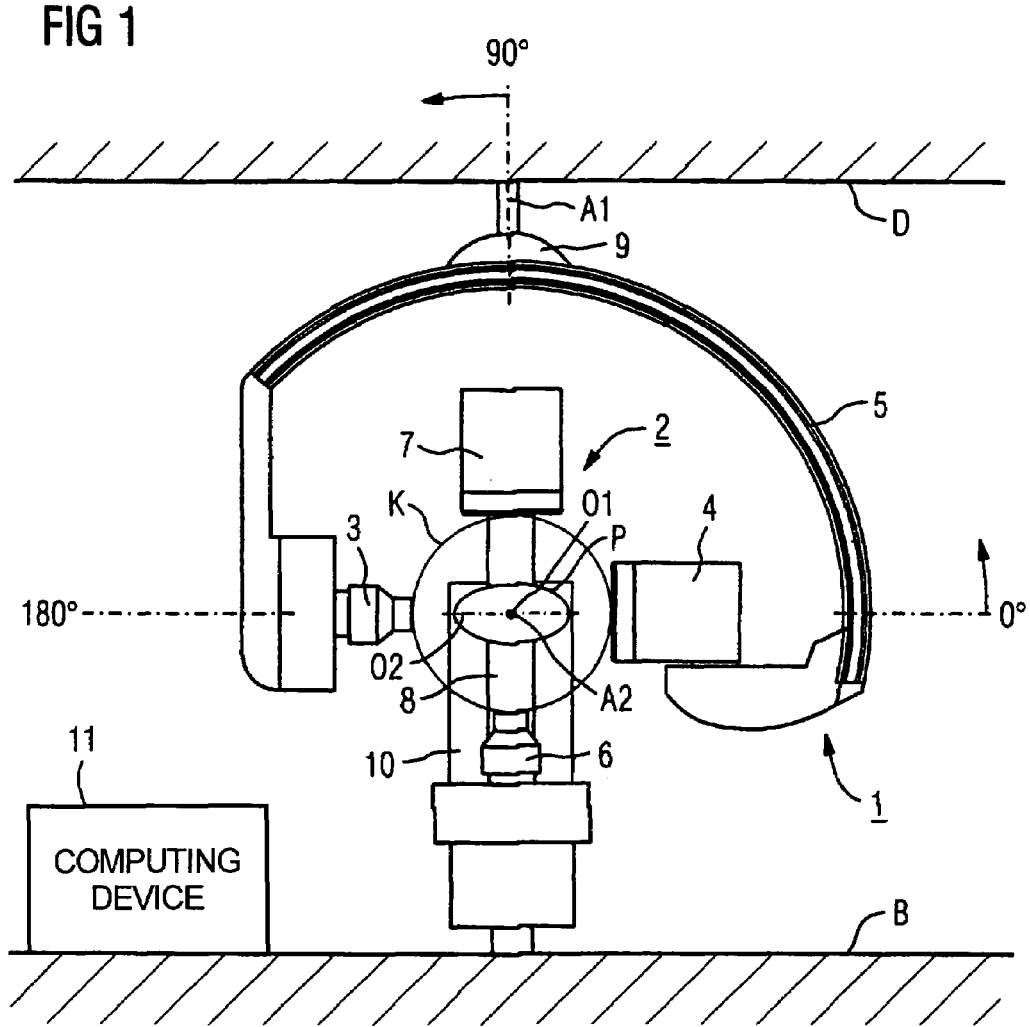

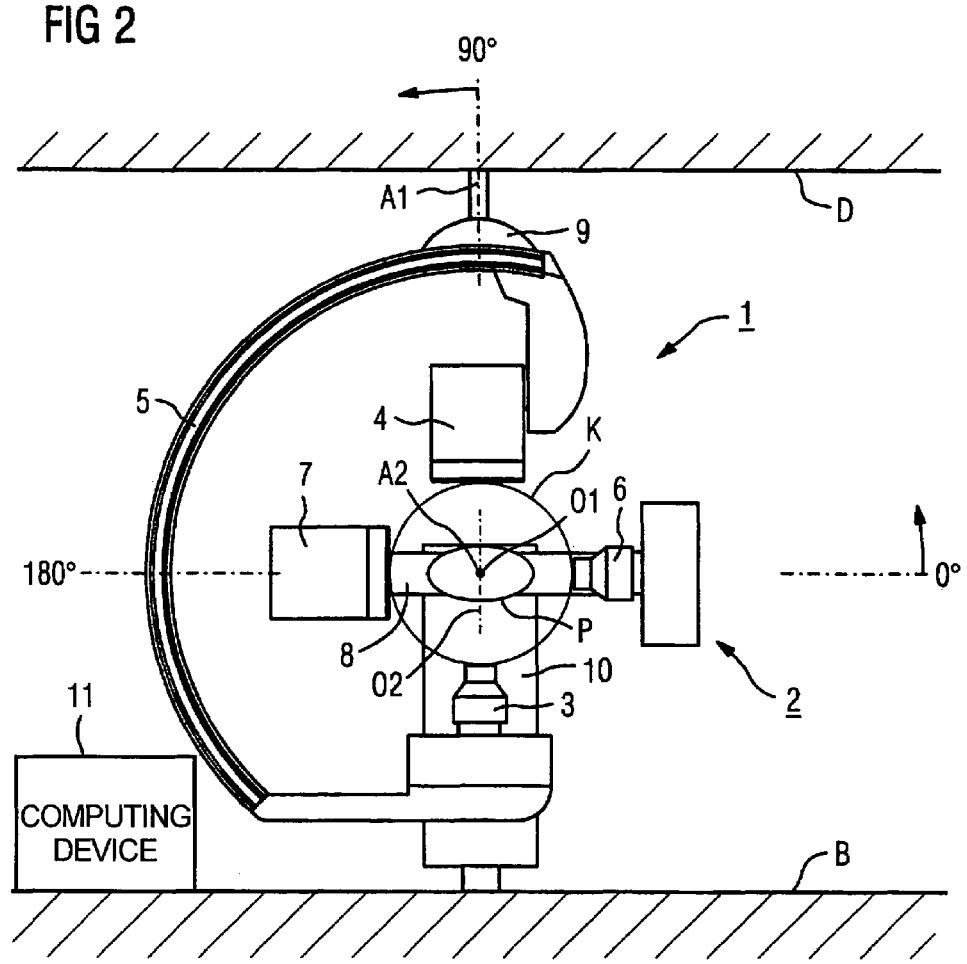

METHOD FOR GENERATING A VOLUME DATASET

BACKGROUND OF THE INVENTION

1. Field of the Invention

The present invention is directed to a method for generating a volume dataset of a subject with an X-ray system having an X-ray source and an X-ray receiver.

2. Description of the Prior Art

A volume dataset of a subject can be generated, for example, with a C-arm X-ray device. To this end, the C-arm provided with an X-ray source and an X-ray receiver is moved around its orbital axis or angulation axis by approximately 180° around the subject, whereby a series of 2D projections is recorded. The 2D projections are acquired from projection angles that differ from one another. Using this series of 2D projections of the subject (which can currently include up to 400 2D projections), a volume dataset of the subject is reconstructed with the assistance of a computer device provided with a reconstruction program and with the assistance of projection geometries for the C-arm X-ray device that were previously determined in a calibration process. 3D images or arbitrarily selectable tomograms of the subject can be calculated from the volume dataset and presented on a display device.

Such a volume dataset of a subject can also be generated with a type of system referred to as a bi-plane system, which is understood to be an X-ray device that has two C-arms each having an with X-ray source and an X-ray receiver mounted thereon. The generation of a volume dataset with a bi-plane system ensues such that one C-arm of the bi-plane system is moved out of the working area while the series of 2D projections of the subject is recorded with the other C-arm, and the volume dataset of the subject is reconstructed therefrom. A disadvantage of this technique for bi-plane systems is that the one C-arm must always be moved out of the work area of the bi-plane system for generating a volume dataset, especially in order to avoid possible collisions with the other C-arm during the acquisition of the series of 2D projections. Another disadvantage is the comparatively lone exposure time required for the acquisition of the series of 2D projections, which is especially disadvantageous in the medical field when a contrast agent must be injected into the body of a patient during the acquisition of the 2D projections in order to be able to show specific tissue regions especially well in the 2D projections.

SUMMARY OF THE INVENTION

An object of the present invention is to provide a method for operating an X-ray device having two X-ray systems with which a volume dataset of a subject can be generated in a shorter time.

This object is achieved in accordance with the invention in a method for generating a volume dataset of a subject with a first X-ray system having an X-ray source and an X-ray receiver and a second X-ray system having an X-ray source and an X-ray receiver that includes the steps of acquiring a first series of 2D projections of the subject, the 2D projections being acquired with the first X-ray system at projection angles differing from one another, by the first X-ray system being rotated around an axis and sweeping a first angular range of substantially X° through Y°, substantially simultaneously acquiring a second series of 2D projections of the subject, the 2D projections being acquired with the second X-ray system at projection angles differing from one another, by rotating the second X-ray system around an axis and sweeping a second angular range of substantially U° through V° differing from the first angular range, and generating a volume dataset of the subject from the first and second series of 2D projections of the subject acquired by the two X-ray systems.

Inventively, thus, 2D projections of a subject from which a volume dataset of the subject can be generated are acquired with not only one X-ray system but in parallel with a second X-ray system. As a result of the parallel acquisition of 2D projections an adequate number of 2D projections of the subject from which a qualitatively high-grade 3D volume dataset can be generated can be acquired in a shorter time compared to conventional methods. As a rule, 2D projections in a total angular range of more than 180° are acquired with the two X-ray systems.

In one version of the invention, the second angular range that the second X-ray system sweeps adjoins the first angular range that the first X-ray system sweeps, so that 2D projections of the subject are recorded over an angular range substantially X° through V°, for example from 0° through 190°. This essentially corresponds to the acquisition of 2D projections in the angular range in which 2D projections are conventionally acquired with one X-ray system in order to be able to reconstruct a volume dataset. Moreover, as already mentioned, the time for the acquisition of the 2D projections is significantly reduced by means of the parallel acquisition of 2D projections with two X-ray systems over respective portions of the overall angular range to be swept. Considering an angular range of approximately 190° that a conventionally operating X-ray system must sweep in order to obtain an adequate number of 2D projections for the reconstruction of a qualitatively high-grade volume dataset, then the time for the acquisition of the 2D projections can be halved when, according to one version of the invention, the first X-ray system sweeps an first angular range from 0° to approximately 95° and the second X-ray system simultaneously sweeps a second angular range from approximately 95° to approximately 190°, that substantially adjoins the first angular range.

In another embodiment of the invention, the first as well as the second X-ray system has a C-arm, each C-arm being provided with an X-ray source and an X-ray receiver. For the substantially simultaneous acquisition of the two series of 2D projections, the C-arms are arranged offset relative to one another, whereby the offset preferably amounting to approximately 90°. This is tailored to the planes defined by the two C-arms.

According to a further version of the invention, the two X-ray systems are rotated with substantially the same angular velocity during the acquisition of the two series of 2D projections. Preferably, the two X-ray systems are rotated around the same axis. Given an offset of the two C-arms by approximately 90°, for example, the one C-arm can be rotated around its angulation axis and the other C-arm can be rotated around its orbital axis. The two X-ray systems preferably move on a circular path.

In a further version of the invention a volume dataset of the subject is reconstructed with the assistance of a computing device, the reconstruction proceeding from the 2D projections of the first and second series of 2D projections of the subject based on previously identified projection geometries for the two X-ray systems.

A further time-saving in the generation of the volume dataset is achieved in an embodiment of the invention wherein a first volume dataset of the subject is reconstructed from the 2D projections of the first series of 2D projections of the subject and a second volume dataset of the subject is reconstructed from the 2D projections of the second series of 2D projections of the subject, the two volume datasets being added to form a resulting volume dataset. The time advantage that is achieved by this manner of generating the volume dataset is based on the reconstructions of the first and of the second volume dataset proceeding with at least some amount of time overlap preferably in parallel.

DESCRIPTION OF THE DRAWINGS

FIG. 1 illustrates an X-ray device having two X-ray systems in an initial position for the implementation of the inventive method.

FIG. 2 illustrates the X-ray device of FIG. 1 is a final position in the implantation of the inventive method.

DESCRIPTION OF THE PREFERRED EMBODIMENTS

In a schematic illustration, FIG. 1 shows an X-ray device for the implementation of the inventive method, a bi-plane X-ray device in the present case. The bi-plane X-ray device has an X-ray system 1 and an X-ray system 2. The X-ray system 1 includes a C-arm 5 provided with an X-ray source 3 and an X-ray receiver 4, and the X-ray system 2 includes a C-arm 8 provided with an X-ray source 6 and an X-ray receiver 8. The X-ray sources 3 and 6 preferably respectively emit conical X-ray beams in the directions of the X-ray receivers 4 and 7, which are X-ray image intensifiers in the present case. Other X-ray receivers, for example flat image detectors, can be utilized instead of X-ray image intensifiers. In the exemplary embodiment, the C-arm 5 is arranged at the ceiling D of a room in which the bi-plane X-ray device is installed and can be rotated around is angulation axis A1 as well as around its orbital axis O1 residing perpendicular to the plane of the drawings. The rotation around the orbital axis O1 ensues by moving the C-arm 5 along its circumference in a holder 9.

The C-arm 8 of the X-ray system 2 is attached via a support (not visible in the drawing) to a housing 10 arranged on a floor B of the room in which the bi-plane X-ray device is installed. In a well-known way, the C-arm 8 can be rotated around its orbital axis O2 indicated in FIG. 1 by means of movement relative to its support and can be rotated together with its support around its angulation axis A2 residing perpendicularly to the plane of the drawing.

In the exemplary embodiments, all rotations of the two C-arms 5 and 8 around their angulation and orbital axes ensue by means of electric motors (not shown), with a connection (not shown) between the electric motors that produce the motion and a computing device 11 being present that controls the electric motors in conformity with data previously entered via a well-known operating device (not shown).

The X-ray systems 1 and 2, the C-arms 5 and 8 thereof in the present exemplary embodiment are arranged offset relative to one another such that the C-arm planes defined by the C-arms 5 and 8 are offset by approximately 9020 relative to one another. As used herein, a C-arm plane mean the plane that passes substantially centrally through the C-arm along its circumference and divides the C-arm into two halves. In the exemplary embodiment, the two C-arms 5 and 8 are also arranged such relative to one another that the orbital axis O1 of the C-arm 5 substantially coincides with the angulation axis A2 of the C-arm 8.

For acquiring two series of 2D projections of a patient P (merely schematically indicated in the FIGS. 1 and 2) at projection angles differing from one another for the reconstruction of a volume dataset of the patient P, the X-ray systems 1 and 2, or the C-arms 5 and 8 thereof in the present exemplary embodiment are electromotively moved around the patient P from their initial position shown in FIG. 1 into their final position shown in FIG. 2. This movement is controlled by the computing device 11. As can be seen from FIG. 1, a first series of 2D projections of the patient P is acquired during the rotation of the X-ray system 1, of the C-arm 5 thereof around its orbital axis O1 from approximately 0° to approximately 90°. The specification of the swept, first angular range from approximately 0° to approximately 90° refers to the X-ray receiver 4 of the X-ray system 1 that is relevant for the imaging. Substantially simultaneously with the X-ray system 1, the X-ray system 2 is likewise rotated around its angulation axis A2 by approximately 90° in the same direction, so the X-ray receiver 7 relevant for the acquisition of the 2D projections in the exemplary embodiment sweeps an angular range from approximately 90° to approximately 180°. The movement of the X-ray system 1 around the orbital axis O1 and the movement of the X-ray system 2 around the angulation axis A2 preferably ensue synchronously and with at least essentially the same angular velocity.

As already mentioned, a first series of 2D projections of the patient P at projection angles that differ from one another is acquired during the movement of the X-ray system 1 through the angular range from approximately 0° to approximately 90°. Simultaneously, a second series of 2D projections of the patient P at projection angles that differ from one another is acquired during the movement of the X-ray system 2 around the angulation axis A2. Since the X-ray system 1 sweeps an angular range from approximately 0° through approximately 90° and the X-ray system 2 sweeps an angular range from approximately 90° through approximately 180°, 2D projections of the patient P in an angular range from approximately 0° through approximately 180° are obtained overall. A volume dataset of the patient P is able to be reconstructed therefrom in the computing device 11 in a well-known way.

The reconstruction of the volume dataset ensues on the basis of projection geometries for the two X-ray systems 1 and 2 that were previously determined in a well-known way in a calibration process and that are stored in a memory (not shown) of the computing device 11. For example, a calibration can ensue with a calibration phantom that is disclosed in German OS 100 47 382 and that has X-ray-positive markers. The position of the calibration phantom relative to the X-ray systems 1 and 2 preferably is not varied in the determination of the projection geometries for the two X-ray systems 1 and 2, so that a registration between the coordinate systems of the two C-arms 5 and 8 can already be produced via the markers shown in the X-ray projection exposures of the calibration phantom. The projection geometries of the two X-ray systems 1 and 2 usually are determined for specific adjustment motions of the X-ray systems 1 and 2. If, thus, the X-ray systems 1 and 2 are to be moved relative to the patient P in a way different from that presently shown in order to be able to acquire 2D projections of the patient P and generate a volume dataset of the patient P, the projection geometries for the two X-ray systems 1 and 2 usually must be re-determined for these adjustment motions in a calibration event, unless the projection geometries belonging to these adjustment motions can be calculated from projection geometries for other adjustment motions that are already known.

Alternatively, a self-calibration is possible, i.e. the determination or calculation of the projection geometries ensues simultaneously with the acquisition of the 2D projections. An appropriate method for self-calibration is described by R. Hartley and A. Zisserman in chapter 18 of Multiple View Geometry in Computer Vision, Cambridge University Press, Cambridge UK, 2000.

According to a first version of the invention, a volume dataset of the patient P is reconstructed from the 2D projections of the patient P acquired in the angular range from approximately 0° to approximately 180° with the X-ray systems 1 and 2 and with the projection geometries of the X-ray systems 1 and 2 determined in the calibration event. The reconstruction takes place in the computing device 11 that is provided with an appropriate reconstruction program.

In another version, a first volume dataset of the patient P can be reconstructed from the 2D projections of the patient P acquired in the angular range from approximately 0° through approximately 90° with the X-ray system 1, and a second volume dataset can be reconstructed with the computing device 11 in parallel thereto from the 2D projections of the patient P acquired over the angular range from approximately 90° through approximately 180° with the X-ray system 2. The two volume datasets reconstructed in parallel are ultimately added by the computing device 11 to form a resulting volume dataset of the patient P. Compared to the first version of the invention, this second version is distinguished by an even faster reconstruction of a resultant volume dataset. For this parallel reconstruction, the computing device 11 can include parallel computers, for example transputers.

Compared to conventional operating systems, each of the two versions allows considerable time to be saved overall in the reconstruction of a volume dataset of a patient P, providing the advantage that the examination time for the patient P is shortened. In radiological exposures upon administration of contrast agent in particular the time for the injection of contrast agent into the patient, and thus the quantity of contrast agent to be injected into the patient can be markedly reduced. Compared to a conventional determination of a volume dataset, the time for the injection of the contrast agent can be lowered by approximately 50% using the procedure described in the exemplary embodiment, which represents an important contribution to more gentle treatment of patients.

In the exemplary embodiment described herein, the X-ray system 1 is moved around its orbital axis O1 and the X-ray system is moved around its angulation axis A2, these axes aligning with one another. Moreover, the X-ray systems 1 and 2, particularly the X-ray receivers 4 and 7, are adjusted on a circular path K. This, however, need not necessarily be the case. The rotational axes of the X-ray systems 1 and 2 may differ from one another, but the deviation from one another must be taken into consideration in the image reconstruction.

Further, the X-ray systems 1 and 2 can be arranged offset relative to one another in some other way or can sweep other angular ranges in the acquisition of series of 2D projections, and these can also overlap. A relationship between the X-ray systems 1 and 2 or between the 2D projections acquired by the X-ray systems 1 and 2 merely has to be produced for the reconstruction of a volume dataset. This preferably already ensues in the calibration of the X-ray systems 1 and 2 in order to be able to acquire a volume dataset of a patient or other of an examination subject from the series of 2D projections that are preferably simultaneously acquired. However, a relationship can also be produced via the computing device 11 that—as control device—knows all positions of the C-arms 5 and 8 relative to one another.

In the described exemplary embodiment, the movements of the X-ray systems 1 and 2 ensue with substantially the same angular velocity. However, the X-ray systems 1 and 2 can be moved with angular velocities that differ from one another. For example, the X-ray system 1 can sweep an angular range from approximately 0° through approximately 120° in a time t, and the X-ray system 2 can sweep an angular range from approximately 120° through approximately 180° in a time t. The time saved in the acquisition of the 2D projections is thus the time that the faster X-ray system needs in order to traverse the smaller angular range of the slower X-ray system.

Moreover, there is also the possibility of acquiring series of 2D projections with the two X-ray systems wherein the two X-ray systems sweep an angular range from 0° through approximately 180° on different circular paths. The duration for the acquisition of the 2D projections is then not shortened, but the quality of the reconstructed volume dataset can be enhanced due to the multitude of 2D projections available for the reconstruction.

Although further modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a volume dataset of a subject comprising the steps of:

mounting a first X-ray system comprising a first x-ray source and a first X-ray receiver, on a first C-arm;

mounting a second X-ray system, comprising a second X-ray source and a second X-ray receiver on a second C-arm:

acquiring a first series of 2D projections in a plane of a subject using a said first X-ray system by irradiating the subject with X-rays emitted by said X-ray source from a plurality of different projection angles while rotating said first C-arm around an axis and sweeping a first angular range of substantially X° through Y°;

substantially simultaneously with acquiring said first series of 2D projections, acquiring a second series of 2D projections in said plane of the subject using said second X-ray system by irradiating the subject with X-rays emitted by said second X-ray source at a plurality of different projection angles while rotating said second C-arm around an axis and sweeping a second angular range of substantially U° through V° differing from said first angular range; and combining said first series of 2D projections and said second series of 2D projections to generate a volume dataset of the subject.

2. A method as claimed in claim 1 comprising rotating said second X-ray system to sweep said second angular range as an angular range that adjoins said first angular range so that said first and second X-ray system, in combination, sweep a total angular range of substantially X° through V°.

3. A method as claimed in claim 1 comprising rotating said first X-ray system to sweep an angular range from approximately 0° to approximately 90° as said first angular range, and rotating said second X-ray system to sweep an angular range from approximately 90° through approximately 180° as said second angular range.

4. A method as claimed in claim 1 comprising orienting said first C-arm and said second C-arm relative to each other to allow said first and second series of 2D projections of the subject to be substantially simultaneously acquired.

5. A method as claimed in claim 4 comprising disposing said first and second C-arms at approximately 90° relative to each other.

6. A method as claimed in claim 1 comprising rotating said first X-ray system and said second X-ray system at respective angular velocities which are substantially equal for respectively acquiring said first and second series of 2D projections.

7. A method as claimed in claim 1 wherein the step of combining said first series of 2D projections and said second series of 2D projections comprises reconstructing said volume dataset from said first and second series of 2D projections.

8. A method as claimed in claim 1 wherein the step of combining said first series of 2D projections and said second series of 2D projections comprises reconstructing a first volume dataset of the subject from the first series of 2D projections, reconstructing a second volume dataset of the subject from said second series of 2D projections, and adding said first volume dataset and said second volume dataset to form said volume dataset of the subject.

9. A method as claimed in claim 8 comprising reconstructing said first volume dataset and said second volume dataset substantially in parallel with each other.

* * * * *